United States Patent
Lazik et al.

(10) Patent No.: US 6,591,862 B1
(45) Date of Patent: Jul. 15, 2003

(54) SYSTEM AND METHOD FOR CARRYING OUT COLUMN TESTS UNDER HYDROSTATIC PRESSURE

(75) Inventors: Detlef Lazik, Halle (DE); Thomas Schneider, Dresden (DE)

(73) Assignee: UFZ-Umweltforschungszentrum Leipzig-Halle GmbH (DE)

( * ) Notice: Subject to any disclaimer, the term of this patent is extended or adjusted under 35 U.S.C. 154(b) by 0 days.

(21) Appl. No.: 09/230,772
(22) PCT Filed: Jul. 28, 1997
(86) PCT No.: PCT/EP97/04085
§ 371 (c)(1),
(2), (4) Date: May 3, 1999
(87) PCT Pub. No.: WO98/05955
PCT Pub. Date: Feb. 12, 1998

(30) Foreign Application Priority Data

Aug. 1, 1996 (DE) .......................... 196 32 388

(51) Int. Cl.[7] ........................ G01N 30/04; G01N 30/36; F17D 3/01
(52) U.S. Cl. ............................ 137/453; 137/2; 137/14; 137/386; 73/61.53; 73/61.55; 73/61.56; 210/198.2
(58) Field of Search .................... 137/1, 2, 8, 9, 137/386, 403, 453, 454; 73/61.52, 61.53, 61.55, 61.56; 210/198.2

(56) References Cited

U.S. PATENT DOCUMENTS

| | | | | |
|---|---|---|---|---|
| 4,960,516 A | * | 10/1990 | Alexandrov et al. | 210/198.2 |
| 5,610,322 A | * | 3/1997 | Un Ger et al. | 73/61.53 |
| 6,033,459 A | * | 3/2000 | Hase | 73/61.52 |

* cited by examiner

Primary Examiner—George L. Walton
(74) Attorney, Agent, or Firm—Norris, McLaughlin & Marcus P.A.

(57) ABSTRACT

A closed $\Delta P_{stat}$-installation is disclosed for the potential-independent control of the pressure difference for continuous column tests under high hydrostatic pressure, as well as a pressure difference control process useful in particular for carrying out migration tests in pressure columns. By coupling two potential bottles into a closed vessel system, the gas or fluid pressure required to carry out the continuous column tests can be regulated at any desired height independently of outer influences. The pressure difference required to move the liquid is adjusted by setting the potential bottles at predeterminable heights.

5 Claims, 2 Drawing Sheets

SYSTEM AND METHOD FOR CARRYING OUT COLUMN TESTS UNDER HYDROSTATIC PRESSURE

BACKGROUND OF THE INVENTION

The invention relates to closed $\Delta P_{stat}$ equipment for the potential-independent control of the pressure gradient for investigations of flow through columns under a high hydrostatic pressure as well as to a method for controlling differential pressure and can be used especially for carrying out migration investigations in pressure columns.

The planning and selection of suitable methods for cleaning up the environment in many cases takes place after extensive investigations on soil and water samples in the laboratory. Dynamic migration experiments in column equipment, which simulates the transport processes, exchange processes and conversion processes in the underground, provide important information for this. They enable cause and effect relationships to be analyzed, so that, for example, the processing of subterranean water or the cleaning up of old polluted areas can frequently be configured optimally with relatively little expense.

When flow and migration processes are simulated in coarse media at high hydrostatic pressures, for example, for describing the migration of pollutants in deep or immense aquifers, the following problem arises: a sufficiently fine harmonization of differential pressures (for example: 1 . . . 200 mbar) and the maintaining of these differences constantly fails at high surrounding pressures (such as 1 . . . 10 bar) as a result of the response accuracy and the switching hysteresis of technical pressure regulating devices.

However, an understanding of migration under extreme pressure conditions can effectively be developed further only if fluids can be driven through porous media at fixed hydrostatic pressures and hydraulically effective pressure gradients within enveloping materials and determined gas composition of fluid (oxygen-free).

The principal of the potential bottle, with which a lamella of fluid (drawn bright) having a height of $\Delta h = h_2 - h_1$ is held above the atmospheric pressure $P_{atm}$ (see FIG. 2), is known. By pulling the small air tube by $dh_2$, the height of the fluid in the open vessel is raised by the same amount $dh_2$. At the same time, the equivalent volume of air flows through the small air tube and collects in the bottle.

The reason for this behavior is as follows. An equipotential surface with the pressure $P(h_2) = P_{atm}$ is formed within the bottle at the height of the air outlet point of the small tube $h_2$ and is maintained by the liquid lamella and air lamella, which are above this equipotential surface and are in equilibrium with atmospheric pressure.

The British patent 2,218,992 A discloses an industrial volume-flow control system, which is to attain a uniform flow through the HPLC column, particularly in the event that the column is built up inhomogeneously. The volume flow on either side of the column and, with that, also at every cross-sectional site within the column, is kept constant here by the controlled addition at the inlet and the controlled removal of solvent at the outlet. The volume flow is controlled by the uniform and oppositely directed change in the solvent volume in the solvent reservoir bottles disposed about the column, the volume change being controlled over a membrane by the volumetric ratio of a working fluid to the bottle volume. Synchronized, oppositely running pumps are used for the control.

Disadvantages of this solution are the relatively high technical effort with active control and regulating components, as well as the separation of the working fluid from the elution fluid by an elastic membrane.

SUMMARY OF THE INVENTION

Utilizing this principle, it is an object of the invention to provide equipment and a method for carrying out column investigations under pressure, with which differential pressures can be harmonized finely and maintained constantly independent of external influences, such as air pressure, air pressure changes, air composition and temperature. Moreover, it shall be possible to manufacture the equipment cost effectively and to operate and maintain it easily.

Pursuant to the invention, this objective is accomplished by the distinguishing features in the characterizing part of claims 1, 6 and 7 in conjunction with the distinguishing features in the introductory portion.

Appropriate developments of the invention are contained in the dependent claims.

A particular advantage of the invention consists therein that the pressure and differential pressure are independent of external influences, such as the composition of the air, any changes in air pressure and the temperature, etc. This is achieved owing to the fact that a closed system of vessels, consisting of at least one column, at least one start potential bottle and at least one target potential bottle, is acted upon with a uniform pressure, and the differential pressure for moving the fluids through the column is produced by the difference between the heights of the fluid in the start potential bottle and the target potential bottle according to the equation $$\Delta h_w = h_B - h_A \text{ with } \Delta P_{stat} = \rho_{fluid} g \, \Delta h_w$$

wherein $\Delta h_w$ —is the effective fluid height difference $h_A$ —is the potential height of the fluid in the start potential bottle $h_B$ —is the potential height of the fluid in the target potential bottle $\Delta P_{stat}$ —is the stationary pressure gradient $\rho_{fluid}$ —is the fluid density g —is the acceleration due to gravity.

The magnitude of the pressure, which can be applied for the simulation of a corresponding hydrostatic pressure, depends only on the technical realization of the system and is designed depending on the objective set. The magnitude of the pressure is not determined by the position or accuracy, with which the differential pressure can be set. Instead, this differential pressure is determined only by the resulting fluid height difference $\Delta h_w$ and the accuracy only by the reading error when $\Delta h_w$ for fluids of a given density is determined, in that at least one start potential bottle is coupled with at least one target potential bottle into a closed system of vessels in such a manner, that a difference between the height of the fluid in the start potential bottle and that in the target potential bottle can be set and the fluid outlet of the start potential bottle is connected with the column inlet and the fluid inlet of the target potential bottle is connected with the column outlet over at least one fluid line and the pressure inlet of the start potential bottle is connected with the pressure inlet of the target potential bottle over at least one pressure line, which is acted upon by one pressure medium.

For higher accuracy requirements, $\Delta h_w$ can be determined directly through the use of sight glasses, which can be mounted on the potential bottles. (Sight glasses can also be used to check the level to which the potential bottles are filled.) Indirectly, an accurate potential equalization is possible by setting the potential difference, at which the fluid transport between at least two (short-circuited) potential bottles barely ceases, equal to zero $$\Delta h_w = 0$$

As fluids, any combination of liquids, capable of forming drops, or gases can be used, which must be unmiscible with one another and have a sufficient density difference. The pressure system can be uncoupled at any time from the sediment-filled column. Valves and optionally self-closing couplings ensure the contamination-free coupling and uncoupling of the system.

By selecting suitable materials and compressed gases, interactions between the technical system and the fluids to be investigated can be precluded for the specific case.

BRIEF DESCRIPTION OF THE DRAWINGS

The invention will be explained in greater detail below by means of examples shown at least partially in the Figures, of which

DESCRIPTION OF THE PREFERRED EMBODIMENTS

Figure 1:
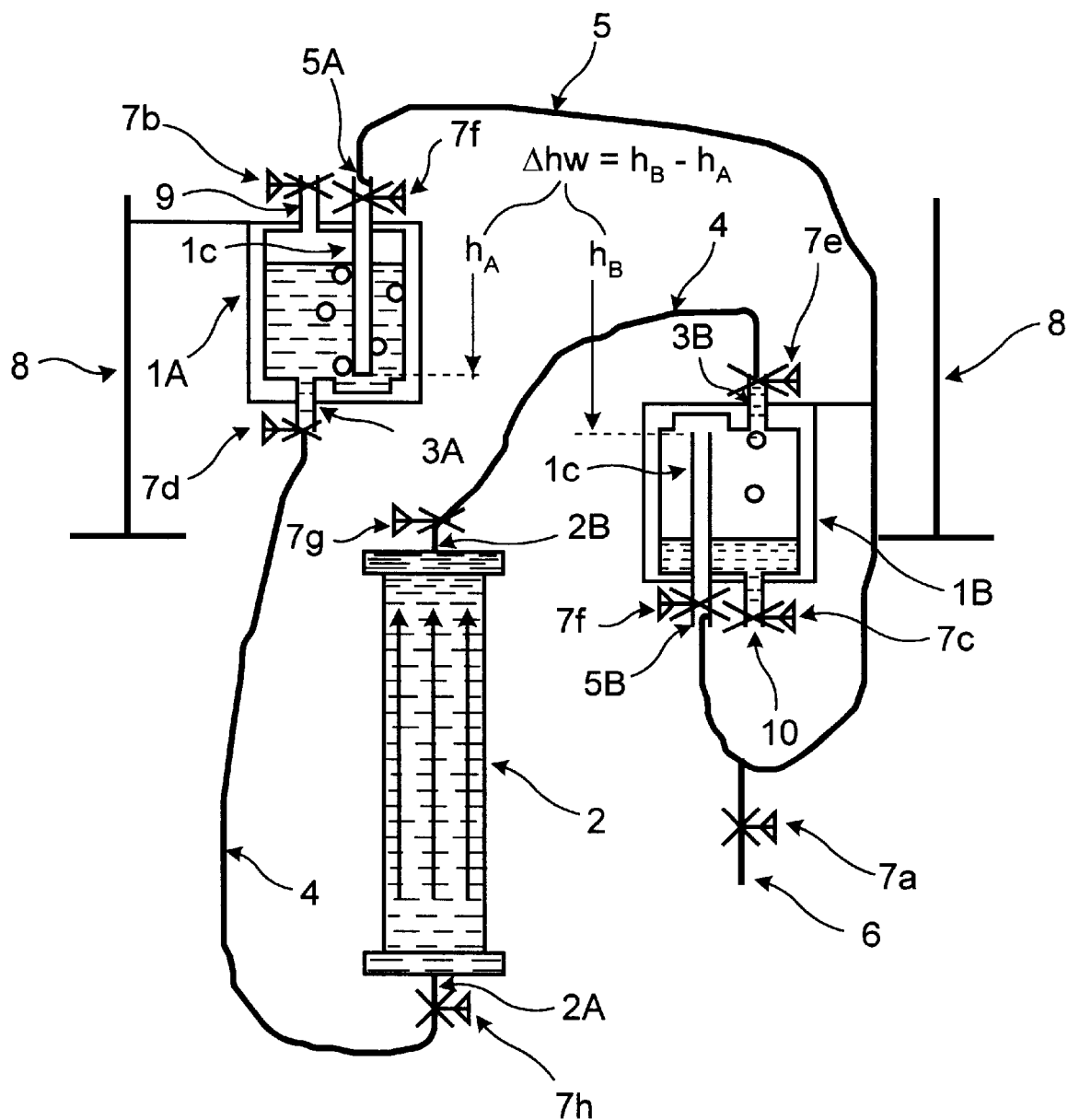
FIG. 1 shows a diagrammatic representation of the closed $\Delta P_{stat}$ equipment for carrying out column investigations under hydrostatic pressure and FIG. 2 shows a diagrammatic representation of the basic physical principle of the potential bottle.
Figure 2:
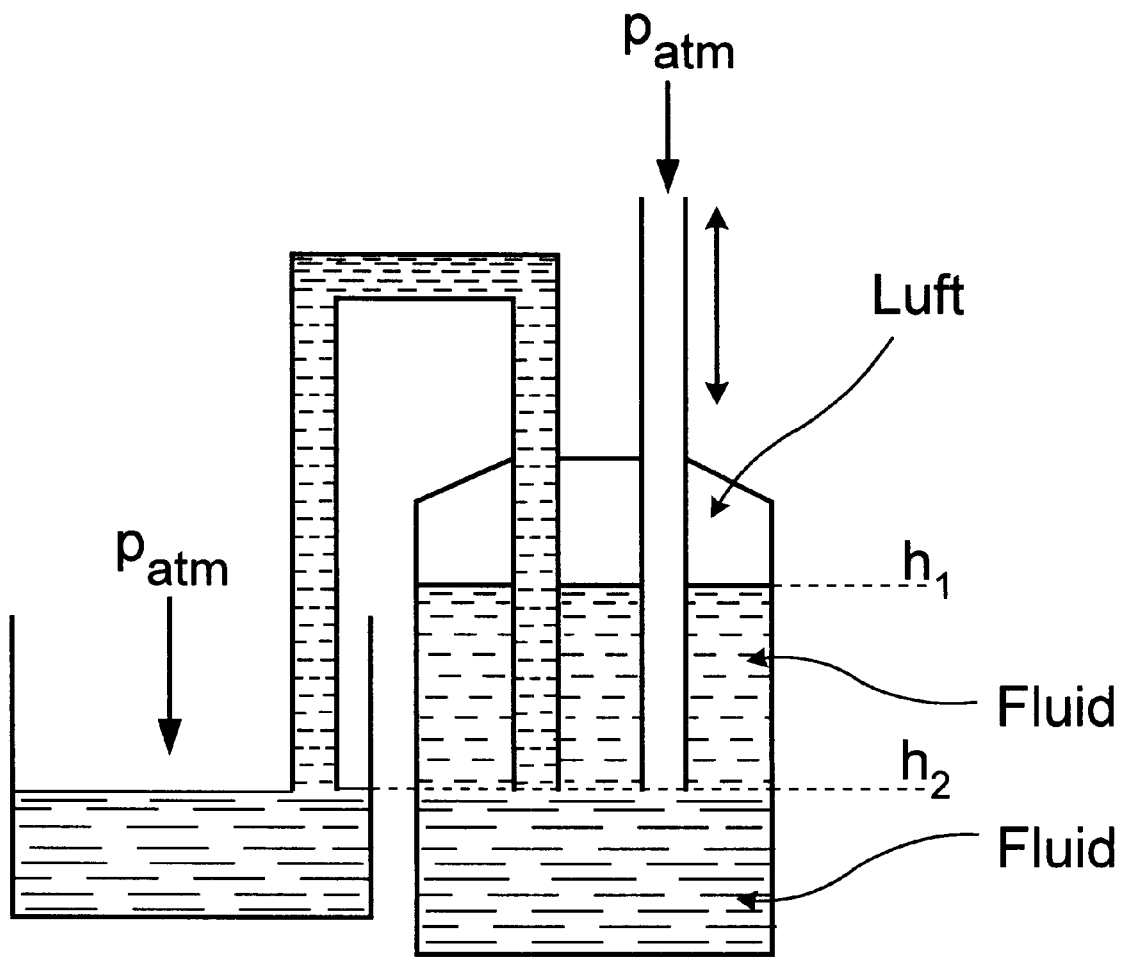

By coupling two potential bottles, as shown in FIG. 1, into a closed system of vessels, it is achieved that the gas pressure or the fluid pressure can be controlled at any level independently of the atmosphere and of external influences, such as air pressure fluctuations, temperature changes, etc. The differential pressure $\Delta P_{stat}$, which is required for moving the liquid in the direction of the potential gradient, is adjusted by adjusting the starting potential bottles 1A and the target potential bottle 1B at heights, which can be fixed corresponding to the effective difference in fluid heights.

$$\Delta h_w = h_B - h_A \text{ with } \Delta P_{stat} = \rho_{fluid} g \Delta h_w$$

($\rho_{fluid}$—density of the fluid, $g$—acceleration due to gravity).

The volume, flowing through the filled column 2, is supplied by the potential-free fluid lamella, standing over $h_A$.

The carrying out of a single elution test is shown in the following. For carrying out a continuous column test, two potential bottle systems, coupled over manifold stopcocks, are required. In each case, one system generates the volume flow of the fluid through the column 2 and the other is filled with new fluid (start potential bottle 1A), or sampled (target potential bottle 1B).

An arrangement with a large start potential bottle 1A and several small target potential bottles 1B, which are connected sequentially over a manifold link, is also possible. In this case, the duration of the investigation is fixed by the size of the start potential bottle 1A and the volumetric resolution capability of the investigation is determined by the size of the target potential bottle 1B.

The dynamic course of the investigation for the single elution described here can be realized as follows. The sediment, either disturbed or undisturbed and either saturated with water or not saturated, is added to the column 2 and the outlet valve 7g and the inlet valve 7h at the column inlet 2A and the column outlet 2B are closed. After that, the potential difference between the start potential bottle 1A and the target potential bottle 1B is adjusted to the desired value by appropriately aligning the bottles on a stand 8. The potential between the two bottles can be equalized in a pressureless preliminary experiment with short-circuited bottles. In the next step, the start potential bottle 1A, including the fluid line 4 to the column 2, is filled through the fluid inlet 9 with the fluid outlet valve 7d open. The compressed gas valve 7f is closed or the gas hose is uncoupled. The fluid inlet valve 7b is now closed and the fluid outlet valve 7c at the target potential bottle 1B is checked to see whether it is closed. The fluid inlet valve 7e at the target potential bottle 1B is now opened. After that, the compressed gas valves 7f at the start potential bottle 1A and the target potential bottle 1B are opened. The outlet valve 7g is now opened at the top at column 2. As the main gas valve 7a is opened, the desired compressed gas pressure in the whole of the system (start potential bottle 1A, column 2, target potential bottle 1B) is now set. The bottles 1A and 1B have small pressure tubes 1C, which are connected with one another through the pressure line 5.

The inlet valve 7h at column 2 is now opened and the elution takes place. At the end of a fixed elution time or elution quantity, the column 2 is uncoupled by closing the inlet valve 7h and the outlet valve 7g on column 2. The pressure on the gas is relieved by opening the fluid inlet 9 with the fluid inlet valve 7b at the start potential bottle 1A. It is now possible to take a sample at the fluid outlet 10 at the target potential bottle 1B and to preserve the fluid. The final step of the column experiment is to open the outlet valve 7g at the column 2 for the purpose of relieving the pressure.

The invention is not limited to the examples described and listed here. Rather, by a combination and modification of the means and distinguishing features mentioned, it is possible to realize further variations of the embodiment, without leaving the confines of the invention.

LIST OF REFERENCE SYMBOLS 1A a start potential bottle
1B target potential bottle
1C small pressure tube
2 column
2A column inlet
2B column outlet
3A fluid column outflow
3B fluid column inflow
4 fluid line
5 pressure line
5A pressure inlet
5B pressure inlet
6 pressure medium
7 valve
7a main gas valve
7b fluid inlet valve
7c fluid outlet valve
7d fluid outlet valve
7e fluid outlet valve
7f compressed gas valves
7g outlet valve
8 stand
9 fluid inlet
10 fluid outlet

What is claimed is:
1. A system for analyzing fluid flow through a packed column, comprising:
at least one start potential vessel, at least one target potential vessel, and at least one column, connected so as to form a closed system, the start potential vessel comprising
a closeable fluid inlet for introducing a fluid to be analyzed,
a fluid outlet opening into the start potential. bottle so as to define a first level at a boundary between the fluid outlet and the interior of the start potential vessel, and
a first pressure pipe extending into the interior of the start potential vessel, and opening within the interior of the start potential vessel at said first level;
the target potential vessel comprising
a closeable fluid outlet for withdrawing a fluid to be analyzed,
a fluid inlet opening into the target potential bottle so as to define a second level at a boundary between the fluid inlet and the interior of the target potential vessel, and
a second pressure pipe extending into the interior of the target potential vessel, and opening within the interior of the target potential vessel at said second level;
a pressure medium for applying pressure to the closed system
the column containing porous media therein through which a fluid to be analyzed will flow, the column comprising
a fluid inlet and a fluid outlet;
the fluid outlet of the start potential vessel being in fluid connection with the fluid inlet of the column,
the fluid outlet of the column being in fluid connection with fluid inlet of the target potential vessel,
the first pressure pipe and the'second pressure pipe being in fluid connection by way of a pressure line,
the means for applying pressure being in fluid connection to the pressure line,
the first level and the second level being adjustable relative to each other, such that when the fluid inlet of the start potential vessel and the fluid oulet of the target potential vessel are closed to thereby effect a closed system, a relative adjustment of the first level and second level acts to independently control the hydraulic pressure for investigation of flow through the column under high hydrostatic pressure.

2. The system of claim 1, wherein the first pressure tube opens downwardly, and the second pressure tube opens upwardly.

3. The system of claim 2, wherein a main portion of a bottom surface of the start potential vessel defines the first level, and the bottom surface has a first reservoir formed as a downward recess in the bottom surface of the start potential vessel, the reservoir residing below the first level, the first pressure pipe extending downward, and opening at the first level at the location of the first reservoir; and wherein
a main portion of a top surface of the target potential vessel defines the second level, and the top surface has a second reservoir formed as an upward recess in the top surface of the target potential vessel, the reservoir residing above the second level, the second pressure pipe extending upward, and opening at the second level at the location of the second reservoir.

4. The system of claim 1, wherein the start potential vessel and the target potential vessel are vertically adjustable relative to each other, so as to effect the relative adjustment of the first level and the second level.

5. A method for controlling the pressure for analysis of fluid flowing through a porous media in a column under high hydrostatic pressure, comprising the steps of:

(1) introducing fluid through a closeable fluid inlet of a closed system, the closed system comprising, in turn,
(a) a start potential vessel, (b) a column, and (c) a target potential vessel,
(a) the start potential vessel comprising
a closeable fluid inlet for introducing a fluid to be analyzed,
a fluid outlet opening into the start potential bottle so as to define a first level at a boundary between the fluid outlet and the interior of the start potential vessel, and
a first pressure pipe extending into the interior of the start potential vessel, and opening within the interior of the start potential vessel at said first level;
(c) the target potential vessel comprising
a closeable fluid outlet for withdrawing a fluid to be analyzed,
a fluid inlet opening into the target potential bottle so as to define a second level at a boundary between the fluid inlet and the interior of the target potential vessel, and
a second pressure pipe extending into the interior of the target potential vessel, and opening within the interior of the target potential vessel at said second level;
a pressure medium for applying pressure to the closed system
(b) the column containing porous media therein through which a fluid to be analyzed will flow, the column comprising
a fluid inlet and a fluid outlet;
the fluid outlet of the start potential vessel being in fluid connection with the fluid inlet of the column,
the fluid outlet of the column being in fluid connection with fluid inlet of the target potential vessel,
the first pressure pipe and the second pressure pipe being in fluid connection by way of a pressure line,
the means for applying pressure being in fluid connection to the pressure line,
the first level and the second level being adjustable relative to each other, such that when the fluid inlet of the start potential vessel and the fluid oulet of the target potential vessel are closed to thereby effect a closed system, an adjustment of the first level with respect to the second level acts to gravimetrically control the hydraulic pressure difference for investigation of flow through the column which is independent of the height of the hydrostatic pressure applied by the pressure medium, and (2) adjusting the differential pressure upon the fluid by adjusting the effective difference ($\Delta h_w$) between a level ($h_A$) of the fluid in the start potential vessel and a level ($h_B$) of the fluid in the target potential vessel, according to the following formula:

$$\Delta h_w = h_B - h_A \text{ with } \Delta P_{stat} = \rho_{fluid} g \Delta h_w,$$

wherein
$\Delta h_w$ is the effective fluid height difference
$h_A$ is the potential height of the fluid in the start potential bottle
$h_B$ is the potential height of the fluid in the target potential bottle
$\Delta P_{stat}$ is the stationary pressure gradient
$\rho_{fluid}$ is the fluid density, and
g is the acceleration due to gravity, and
(3) withdrawing a fluid to be analyzed.

* * * * *